United States Patent [19]

Rohr

[11] 4,047,931
[45] Sept. 13, 1977

[54] PROCESS FOR THE CONTROL OF PLANT METABOLISM

[75] Inventor: Otto Rohr, Therwil, Switzerland

[73] Assignee: Ciba-Geigy Corporation, Ardsley, N.Y.

[21] Appl. No.: 638,409

[22] Filed: Dec. 8, 1975

Related U.S. Application Data

[62] Division of Ser. No. 462,146, April 29, 1974, Pat. No. 3,944,411, which is a division of Ser. No. 239,328, March 29, 1972, Pat. No. 3,821,285.

[30] Foreign Application Priority Data

Apr. 1, 1971 Switzerland .......................... 4775/71

[51] Int. Cl.$^2$ ................................................ A01N 9/24
[52] U.S. Cl. ......................................................... 71/107
[58] Field of Search ........................ 71/107, 106, 115; 260/474, 476 R; 424/230

[56] References Cited

U.S. PATENT DOCUMENTS

| 1,627,342 | 5/1927 | Sabalitschka | 424/230 |
| 2,474,005 | 6/1949 | Martin et al. | 260/474 |
| 3,336,131 | 8/1967 | Weil et al. | 71/107 |
| 3,644,424 | 2/1972 | Sherlock | 260/474 |

OTHER PUBLICATIONS

Farbwerke, "Halogen alkyl esters of aromatic, etc.;" (1924) CA 18 p. 841 (1924).
Ihndris et al., "Effect of Promising Insect Repellents etc.;" (1955) CA 49 p. 16318 (1955).

Primary Examiner—Glennon H. Hollrah
Attorney, Agent, or Firm—Harry Falber

[57] ABSTRACT

Halogenethyl esters of aromatic carboxylic acids are useful ingredients to influence plant metabolism. They may be used preferably for regulating fruit abscission.

1 Claim, No Drawings

PROCESS FOR THE CONTROL OF PLANT METABOLISM

This is a division of Ser. No. 462,146, filed on Apr. 29, 1974, now U.S. Pat. No. 3,944,411 which, in turn, is a division of application Ser. No. 239,328, filed on Mar. 29, 1972, now U.S. Pat. No. 3,821,285.

The present invention relates to a process for the control of plant metabolism with the aid of halogenethyl esters of aromatic carboxylic acids corresponding to the general formula I:

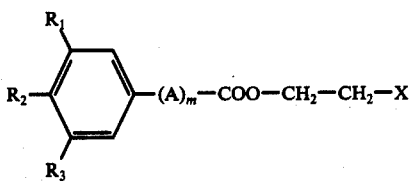

(I)

The symbols in this formula have the following meanings:

$R_1$ represents hydrogen, lower alkyl, lower alkoxy, lower halogenalkyl, nitro, halogen, or the group $R_4OCO-$ wherein $R_4$ represents alkyl, halogenalkyl, substituted or unsubstituted phenyl, $R_2$ represents hydrogen, halogen, lower alkoxy, lower alkyl, $R_3$ represents hydrogen, lower alkoxy, A represents the methylene group, the vinylene group ($-CH=CH-$) or lower oxyalkylene, X represents chlorine, bromine or iodine, and m represents the number 0 or 1.

By lower alkyl is meant, according to the above definitions, straight-chain or branched radicals having 1 to 4 carbon atoms, e.g. methyl, ethyl, n-propyl, isopropyl, n-butyl, isobutyl, sec-butyl or tert-butyl. These lower alkyl radicals constitute also the alkyl moiety of an alkoxy radical, or of an alkanoyloxy radical ($R_4OCO-$). Trifluoromethyl is preferred as halogenalkyl; but methyl or ethyl radicals mono- or polysubstituted by chlorine and/or fluorine are also suitable. By halogen, denoted by $R_1$ and/or $R_2$, are meant, independently of each other, fluorine, chlorine, bromine and/or iodine atoms. A phenyl radical $R_4$ can be mono- or polysubstituted by lower alkyl, lower alkoxy or halogenalkyl, and/or by halogen such as fluorine, chlorine, bromine or iodine.

The halogenethyl esters of aromatic carboxylic acids of formula I are produced by the reaction of a carboxylic acid derivative of formula II:

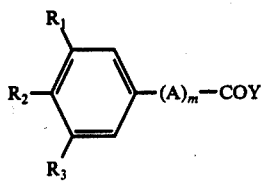

(II)

with a compound of formula III:

$$Z-CH_2-CH_2-X \qquad (III)$$

The symbols $R_1$, $R_2$, $R_3$, A, m and X in these formulae have the meanings given under formula I, while Y and Z represent reactive radicals, and both stand for the hydroxyl group, or one of them represents a halogen atom and the other an optionally metallised hydroxyl group $-OH$ or $O-Me$, wherein Me denotes a mobile metal cation which can be split off, e.g. an alkali metal cation, or the equivalent of an alkaline-earth metal cation.

It is advantageous if the reaction is performed in the presence of a solvent or diluent inert to the reactants; suitable solvents or diluents for this purpose are, e.g. hydrocarbons such as benzene, toluene or xylenes, halogenated hydrocarbons such as chlorobenzene, methylene chloride, ethylene chloride, chloroform, carbon tetrachloride, N,N-dialkylated amides such as dimethylformamide, also ethers and ethereal compounds such as dialkyl ether, dioxane, tetrahydrofuran, or, in the case where Y and Z each represent OH, the corresponding halogenated ethanol. If $Y=Z=OH$, or if one of the two symbols represents OH and the other halogen, then the process can be carried out in the presence of an anhydrous acid or base. Suitable acids are, e.g. the following: hydrohalic acids, sulphuric acid, etc., and suitable bases are, e.g. inorganic bases such as alkali metal hydroxides and alkaline-earth metal hydroxides or -oxides; and organic bases such as tertiary amines.

In the preferred embodiment of the process, a carboxylic acid halide, preferably the chloride or bromide, is reacted, as the carboxylic acid derivative of formula II, with a 2-halogenethanol ($X-CH_2-CH_2OH$) in the presence of a solvent, preferably benzene.

Halogenethyl esters of aromatic carboxylic acids of formula I affect, in a varying manner, the growth of parts of plants above and below the soil; the compounds have a low toxicity towards warm-blooded animals. The active substances cause no morphological changes or damage which would result in the withering of the plant. Their action is different from that of a herbicidal active substance and from that of a fertiliser. The new compounds affect the germination power and the vegetative plant growth, and promote blossom formation, fruit ripening and the formation of abscission layers.

By virtue of their effectiveness, the halogenethyl esters of special importance are those corresponding to formula IV:

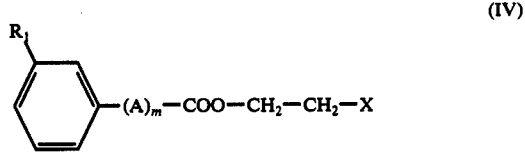

(IV)

The symbols $R_1$, A, m and X in this formula have the meanings defined under formula I. Compounds having a particularly gentle effect on plant metabolism are those compounds of formula I wherein X = iodine. The invention relates also to these new compounds of formula Ia:

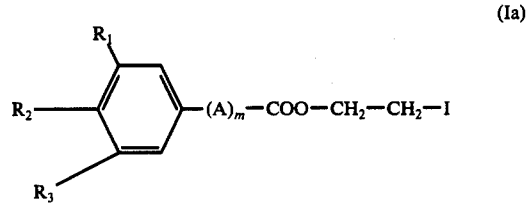

(Ia)

wherein $R_1$, $R_2$, $R_3$, A and m have the meanings given for formula I, as well as to the process for their production by the method given for formula I, and also to agents affecting plant metabolism which contain these compounds of formula Ia as active substances.

Compounds particularly suitable for the promotion of fruit and leaf abscission are compounds of formula V:

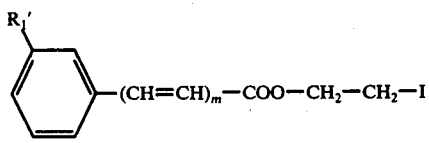

wherein
$R_1'$ represents hydrogen, halogen, trifluoromethyl, acetoxy or lower alkyl, and
m represents the number 0 or 1.

2'-Fluoroethyl esters of aromatic carboxylic acids are known from the literature as insecticidal and acaricidal active substances (cp. the German Offenlegungsschrift 1,808,938). The compounds are phytotoxic and have a high toxicity towards warm-blooded animals.

The following example serves to illustrate the process according to the invention. The table following the example contains further halogenethyl esters of aromatic carboxylic acids of formula I, which were obtained in the manner described in the said example. The temperatures are expressed in degrees Centigrade, and the pressure in Torr (1 Torr = 1 mm Hg).

EXAMPLE 1

An amount of 20 g of 3-acetoxybenzoyl chloride is dissolved in 200 ml of benzene, and 17.5 g of iodoethanol added. An addition is subsequently made dropwise at 15° – 25°, with cooling and vigorous stirring, of 12 g of triethylamine; the organic phase is dried over sodium sulphate, and the solvent distilled off. The oily residue is distilled in high vacuum. 3-Acetoxybenzoic acid-(2'-iodoethyl)-ester passes over at 145°–153°/0.05 Torr.

| Compounds | Physical data | |
|---|---|---|
| 3-acetoxybenzoic acid-(2'-bromoethyl)-ester | M.P. | 49°–52° |
| 3-acetoxybenzoic acid-(2'-chloroethyl)-ester | M.P. | 52°–54° |
| benzoic acid-(2'-iodoethyl)-ester | B.P. | 87°/0.02 |
| 3-chlorobenzoic acid-(2'-iodoethyl)-ester | B.P. | 95°/0.015 |
| 3-bromobenzoic acid-(2'-iodoethyl)-ester | $n_D^{20}$: | 1.6050 |
| 3-trifluoromethylbenzoic acid-(2'-iodoethyl)-ester | B.P. | 85°/0.02 |
| 3-methylbenzoic acid-(2'-iodoethyl)-ester | B.P. | 96°/0.01 |
| 3-methoxybenzoic acid-(2'-iodoethyl)-ester | $n_D^{23}$: | 1.5730 |
| 3,5-dimethoxybenzoic acid-(2'-iodoethyl)-ester | $n_D^{23}$: | 1.5317 |
| 3,4-dimethylbenzoic acid-(2'-iodoethyl)-ester | $n_D^{23}$: | 1.5710 |
| 4-methoxybenzoic acid-(2'-iodoethyl)-ester | B.P. | 138°/0.03 |
| 3,4-dimethoxybenzoic acid-(2'-iodoethyl)-ester | M.P. | 75°–77° |
| cinnamic acid-(2'-iodoethyl)-ester | $n_D^{20}$: | 1.6164 |
| 3,5-dimethoxybenzoic acid-(2'-chloroethyl)-ester | M.P. | 50°–52° |
| 3,5-dimethoxybenzoic acid-(2'-bromoethyl)-ester | $n_D^{27}$: | 1.5406 |
| 3-fluorobenzoic acid-(2'-iodoethyl)-ester | B.P. | 98°/0.035 |
| 3-chlorobenzoic acid-(2'-chloroethyl)-ester | B.P. | 147°/10 |
| 3-chlorobenzoic acid-(2'-bromoethyl)-ester | B.P. | 158°/10 |
| 3-bromobenzoic acid-(2'-chloroethyl)-ester | B.P. | 160°/10 |
| 3-bromobenzoic acid-(2'-bromoethyl)-ester | B.P. | 173°/10 |
| 3-trifluoromethylbenzoic acid-(2'-chloroethyl)-ester | B.P. | 73°/0.03 |
| 3-trifluoromethylbenzoic acid-(2'-bromoethyl)-ester | B.P. | 82°/0.03 |
| 3-methylbenzoic acid-(2'-chloroethyl)-ester | B.P. | 175°/10 |
| 3-methylbenzoic acid-(2'-bromoethyl)-ester | B.P. | 151°/10 |
| 3-nitrobenzoic acid-(2'-iodoethyl)-ester | B.P. | 135°/0.023 |

-continued

| Compounds | Physical data | |
|---|---|---|
| 3-nitrobenzoic acid-(2'-bromoethyl)-ester | B.P. | 125°/0.025 |
| 3-nitrobenzoic acid-(2'-chloroethyl)-ester | B.P. | 130°/0.03 |
| 3,4-dichlorobenzoic acid-(2'-iodoethyl)-ester | M.P. | 52°–54° |
| 3,4-dichlorobenzoic acid-(2'-bromoethyl)-ester | M.P. | 42°–44° |
| 3,4-dichlorobenzoic acid-(2'-chloroethyl)-ester | M.P. | 32°–34° |
| cinnamic acid-(2'-chloroethyl)-ester | B.P. | 118°/0.05 |
| cinnamic acid-(2'-bromoethyl)-ester | B.P. | 116°/0.03 |
| phenoxyacetic acid-(2'-iodoethyl)-ester | B.P. | 108°/0.05 |
| phenylacetic acid-(2'-iodoethyl)-ester | B.P. | 98°/0.03 |
| α-phenoxypropionic acid-(2'-iodoethyl)-ester | B.P. | 109°/0.065 |
| 3-trifluoroacetoxybenzoic acid-(2'-iodoethyl)-ester | | oil |
| 3-benzoylbenzoic acid-(2'-iodoethyl)-ester | | oil |
| 3-(m-chlorobenzoyloxy)-benzoic acid-(2'-iodoethyl)-ester | | oil |

The active substances of formula I promote, in particular, the formation of abscission layers between stalk and fruit stems. Consequently, fruit of every kind, such as, e.g. citrus fruits, stone fruit, berries, grape vines, pomaceous or oil fruits, can be picked without any great applicatin of force, either by hand or with machines developed for the purpose. Damage to the foliage and branches of the tree or bush usually occurring on gathering of the crop as a result of the violent shaking of the trees or bushes, or the tearing off of the fruit, is largely avoided.

The extent and the nature of the action are dependent on the most diverse factors, depending on the variety of the plant; they are dependent, in particular, on the applied concentration, and on the time of application with regard to the stage of development of the plant and of the fruit. Thus, for example, plants of which the fruit is processed or sold will be treated immediately after blossoming, or at a suitable point of time before the gathering of the crop. The active substances are preferably applied in the form of liquid agents to parts of plants above the soil, into the soil, or onto the surface of the soil. Application to parts of the plants above the soil is preferred, for which application solutions or aqueous dispersions are best suited.

The following tests show the action of the new compounds as abscission agents.

EXAMPLE 2

Segments of bean leaves of the variety "Tempo" or their stems were immersed in solutions containing 10 and 20 ppm of active substance, respectively. In the case of each active substance, 8 leaf segments or their stems were left for 5 days under controlled conditions in the active substance solution. The number of occurred abscissions was afterwards determined.

| Evaluation: | 1 = no abscission<br>2 = abscission on 2 segments<br>3 = abscission on 4 segments<br>4 = abscission on 6 segments<br>5 = abscission on 8 segments | |
|---|---|---|
| Active substance | 10 ppm | 20 ppm |
| 3,5-dimethoxybenzoic acid-(2'-iodoethyl)-ester | 3.5 | 4 |
| 3-bromobenzoic acid-(2'-iodoethyl)-ester | 4.5 | 5 |
| cinnamic acid-(2'-iodoethyl)-ester | 4.5 | 4.5 |
| benzoic acid-(2'-iodoethyl)-ester | 5 | 4 |
| 3-chlorobenzoic acid-(2'-iodoethyl)-ester | 5 | 5 |
| 3-trifluoromethylbenzoic acid-(2'-iodoethyl)-ester | 5 | 5 |
| 3-methylbenzoic acid-(2'-iodoethyl)-ester | 5 | 4.5 |
| 3-acetoxybenzoic acid-(2'-iodoethyl)- | | |

-continued

| | | |
|---|---|---|
| Evaluation: | 1 = no abscission<br>2 = abscission on 2 segments<br>3 = abscission on 4 segments<br>4 = abscission on 6 segments<br>5 = abscission on 8 segments | |
| Active substance | 10 ppm | 20 ppm |
| ester | — | 5 |

EXAMPLE 3

On orange trees of the mentioned variety, individual branches carrying at least 15–20 ripe oranges were sprayed with an active substance concentration of 0.4% and of 0.2%. The picking force required in the case of 10 identically treated oranges was measured 7 days after application, with the aid of a spring balance, and the mean value of the 10 measurements calculated [W. C. Wilson and C. H. Hendershott, Proc. Am. Soc. Hort. Science 90, 123–129 (1967)].

The active substances of formula I produced in this test the percentage reductions in picking force, compared with values obtained with untreated trees, listed in the following table:

| Active substance | Concentration in % | Reduction in picking force % | Variety |
|---|---|---|---|
| phenylacetic acid-(2'-iodo-ethyl)-ester | 0.4<br>0.2 | 95<br>30 | 1 |
| benzoic acid-(2'-iodoethyl)-ester | 0.4 | 57 | 1 |
| 3-chlorobenzoic acid-(2'-iodo-ethyl)-ester | 0.4<br>0.2 | 73<br>60 | 1 |
| 3-bromobenzoic acid-(2'-iodo-ethyl)-ester | 0.4<br>0.2 | 72<br>56 | 1 |
| 3-acetoxybenzoic acid-(2'-iodoethyl)-ester | 0.4<br>0.2 | 95<br>73 | 2 |

Varieties:
1 = Hamlin
2 = Temple

Abscission agents according to the invention are produced in a manner known per se by the intimate mixing and grinding of active substances with suitable carriers, optionally with the addition of dispersing agents or solvents which are inert to the active substances. The active substances can be obtained and used in the following forms:
  solid preparations: dusts, scattering agents, granulates, (coated granulates, impregnated granulates and homogeneous granulates);
  water-dispersible concentrates of the active substance: wettable powders, pastes, emulsions;
  liquid preparations: solutions.

The solid preparations (dusts, scattering agents, granulates) are produced by the mixing of the active substances with solid carriers. Suitable carriers are, e.g. kaolin, talcum, bole, loess, chalk, limestone, ground limestone, Attaclay, dolomite, diatomaceous earth, precipitated silicic acid, alkaline-earth silicates, sodium and potassium aluminum silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm; for scattering agents from about 0.075 mm to 0.2 mm; and for granulates 0.2 mm or coarser.

The concentrations of active substance in the solid preparation forms are from 0.5 to 80%.

To these mixtures may also be added additives stabilising the active substance, and/or non-ionic, anion-active, and cation-active substances, which, for example, improve the adhesiveness of the active substances on plants and on parts of plants (adhesives and agglutinants), and/or ensure a better wettability (wetting agents) and dispersibility (dispersing agents). Suitable adhesives are, for example, the following: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acids, their alkali metal and alkaline-earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, as well as latex products.

Water-dispersible concentrates of active substance, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents. The concentration of active substance in these agents is 5 to 80%.

The wettable powders and the pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylaryl sulphonate, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkali-metal and alkaline-earth metal salts.

Suitable anti-foam agents are, for example, silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents, and water. Suitable solvents are, e.g. the following: alcohols, benzene, xylenes, toluene, dimethylsulphoxide, N,N-dialkylated amides, N-oxides of amines, particularly trialkylamines, and mineral oil fractions boiling in the range of 120° to 350°. The solvents must be practically odourless, non-phytotoxic, inert to the active substances, and not readily inflammable.

Furthermore, the agents according to the invention can be applied in the form of solutions. For this purpose the active substance (or several active substances) is (or are) dissolved in suitable organic solvents, mixtures of solvents, water, or mixtures of organic solvents with water. It is possible to use as organic solvents: aliphatic and aromatic hydrocarbons, their chlorinated derivatives, alkylnaphthalenes, mineral oils on their own or in admixture with each other. The solutions are to contain the active substances in a concentration of from 1 to 20%. These solutions can be applied with the aid of a propellent gas (as spray), or by means of special sprayers (such as aerosol).

Other biocidal active substances or agents may be added to the described agents according to the invention. For the supplementing or broadening of their sphere of action, the new agents can also contain, in addition to the stated compounds of the general formula I, e.g. insecticides, herbicides, fungicides, bactericides, fungistatics, bacteriostatics or nematocides. The agents according to the invention can also contain fertilisers, trace elements, etc..

Preparations of the new active substances are described in the following. The term 'parts' denotes parts by weight.

WETTABLE POWDERS

The following constituents are used for the preparation of (a) a 50%, (b) a 25% and (c) a 10% wettable powder:

(a)

50 parts of 3,5-dimethoxybenzoic acid-(2'-iodoethyl)-ester,
5 parts of alkylarylsulphonate,
10 parts of calcium lignin sulphonate,
1 part of Champagne chalk/ hydroxyethyl cellulose mixture (1:1),
20 parts of silicic acid,
14 parts of kaolin;

(b)

25 parts of cinnamic acid-(2'-iodoethyl)-ester,
5 parts of the sodium salt of oleylmethyl tauride,
2.5 parts of naphthalenesulphonic acid/formaldehyde condensate,
0.5 part of carboxymethyl cellulose,
5 parts of neutral potassium-aluminium-silicate,
62 parts of kaolin;

(c)

10 parts of 3-acetoxybenzoic acid-(2'-iodoethyl)-ester,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; and the mixture is then ground by means of suitable mills and rollers. Wettable powders are obtained which can be diluted with water to obtain suspensions of any desired concentration.

EMULSION CONCENTRATE

The following constituents are mixed together for the preparation of a 25% emulsion concentrate:

(a)

25 parts of 3-bromobenzoic acid-(2'-iodoethyl)-ester,
5 parts of a mixture of nonylphenolpolyoxyethylene and calcium-dodecylbenzene sulphonate,
70 parts of xylene.

This concentrate can be diluted with water to obtain emulsions of suitable concentration. Such emulsions are suitable for the accelerated ripening of fruits, and for the promotion of fruit and leaf abscission.

Instead of the active substances mentioned for the production of the wettable powders and the emulsion concentrate, it is also possible to use the other compounds embraced by formula I.

I claim:
1. A process for the promotion of fruit abscission which comprises applying to the fruit-bearing plant or to the fruit itself an effective, non-phytotoxic amount of 3-acetoxybenzoic acid -(2'-iodoethyl)-ester.

* * * * *